United States Patent
Srinivasan et al.

(10) Patent No.: US 9,625,430 B2
(45) Date of Patent: Apr. 18, 2017

(54) MULTIELECTRODE ELECTROLYTIC DEVICE AND METHOD

(71) Applicant: DIONEX CORPORATION, Sunnyvale, CA (US)

(72) Inventors: Kannan Srinivasan, Tracy, CA (US); Sheetal Bhardwaj, Fremont, CA (US); Rong Lin, Santa Clara, CA (US)

(73) Assignee: DIONEX CORPORATION, Sunnyvale, CA (US)

( * ) Notice: Subject to any disclaimer, the term of this patent is extended or adjusted under 35 U.S.C. 154(b) by 488 days.

(21) Appl. No.: 14/057,864

(22) Filed: Oct. 18, 2013

(65) Prior Publication Data

US 2015/0111305 A1    Apr. 23, 2015

(51) Int. Cl.
| | |
|---|---|
| *G01N 30/00* | (2006.01) |
| *G01N 30/96* | (2006.01) |
| *B01D 15/36* | (2006.01) |
| *B01D 61/44* | (2006.01) |
| *G01N 30/64* | (2006.01) |

(52) U.S. Cl.
CPC ........... *G01N 30/96* (2013.01); *B01D 15/367* (2013.01); *B01D 61/44* (2013.01); *G01N 2030/645* (2013.01); *G01N 2030/965* (2013.01)

(58) Field of Classification Search
CPC ................................ G01N 30/96; B01D 61/44
USPC ........................................... 436/161; 210/638
See application file for complete search history.

(56) References Cited

U.S. PATENT DOCUMENTS

| | | | |
|---|---|---|---|
| 3,897,213 | A | 7/1975 | Stevens et al. |
| 3,920,397 | A | 11/1975 | Small et al. |
| 3,925,019 | A | 12/1975 | Hamish et al. |
| 3,926,559 | A | 12/1975 | Stevens |
| 4,265,634 | A | 5/1981 | Pohl |
| 4,403,039 | A | 9/1983 | Ban et al. |
| 4,459,357 | A | 7/1984 | Jansen et al. |
| 4,474,664 | A | 10/1984 | Stevems et al. |
| 4,486,312 | A | 12/1984 | Slingsby et al. |
| 4,751,004 | A | 6/1988 | Stevens et al. |
| 4,999,098 | A | 3/1991 | Pohl et al. |
| 5,045,204 | A | 9/1991 | Dasgupta et al. |
| 5,248,426 | A | 9/1993 | Stillian et al. |

(Continued)

FOREIGN PATENT DOCUMENTS

| | | |
|---|---|---|
| CN | 102141559 | 8/2011 |
| CN | 102253163 | 11/2011 |

(Continued)

OTHER PUBLICATIONS

Srinivasan et a., "Suppressor Design and Detection for ion Chromatography" in: "Applications of Ion Chromatography for Pharmaceutical and Biological Products," Mar. 9, 2012, John Wiley & Sons, Inc., pp. 91-105.*

*Primary Examiner* — Christopher A Hixson
*Assistant Examiner* — Emily Berkeley

(57) ABSTRACT

An electrolytic device comprising: a central sample flow channel, first and second regenerant flow channels, first and second charged barriers disposed between said sample flow channel and first and second regenerant flow channels, and pairs of oppositely charged, spaced electrodes disposed in the regenerant flow channels. Also, electrolytic devices with a different electrode configuration are described. Also, methods of using the devices, e.g., for suppression in an ion chromatography system are described.

23 Claims, 10 Drawing Sheets

(56) References Cited

U.S. PATENT DOCUMENTS

| | | |
|---|---|---|
| 5,352,360 A | 10/1994 | Stillian et al. |
| 5,376,240 A | 12/1994 | Kaczur et al. |
| 5,518,622 A | 5/1996 | Stillian et al. |
| 5,597,481 A | 1/1997 | Stillian et al. |
| 5,759,405 A | 6/1998 | Anderson, Jr. et al. |
| 6,077,434 A * | 6/2000 | Srinivasan ............. G01N 30/96 204/520 |
| 6,200,477 B1 | 3/2001 | Anderson, Jr. et al. |
| 6,610,546 B1 | 8/2003 | Liu et al. |
| 6,686,751 B1 | 2/2004 | Saito et al. |
| 6,752,927 B2 | 6/2004 | Srinivasan et al. |
| 6,808,608 B2 | 10/2004 | Srinivasan et al. |
| 7,399,415 B2 | 7/2008 | Srinivasan et al. |
| 7,618,535 B2 | 11/2009 | Srinivasan et al. |
| 7,618,826 B2 | 11/2009 | Liu et al. |
| 7,892,848 B2 | 2/2011 | Riviello |
| 7,981,284 B2 | 7/2011 | Sakamoto et al. |
| 8,129,194 B2 | 3/2012 | Riviello |
| 8,293,099 B2 | 10/2012 | Dasgupta et al. |
| 8,551,318 B2 | 10/2013 | Dasgupta et al. |
| 2004/0048389 A1 | 3/2004 | Liu et al. |
| 2006/0231404 A1 | 10/2006 | Riviello |
| 2008/0069731 A1 | 3/2008 | Liu et al. |
| 2009/0218238 A1 | 9/2009 | Dasgupta et al. |
| 2010/0320132 A1 | 12/2010 | Sakamoto et al. |
| 2013/0048498 A1 | 2/2013 | Dasgupta et al. |

FOREIGN PATENT DOCUMENTS

| | | |
|---|---|---|
| EP | 2402291 B1 | 6/2013 |
| JP | 2013195301 | 9/2013 |
| WO | 9938595 | 8/1999 |
| WO | 02071052 A2 | 9/2002 |

\* cited by examiner

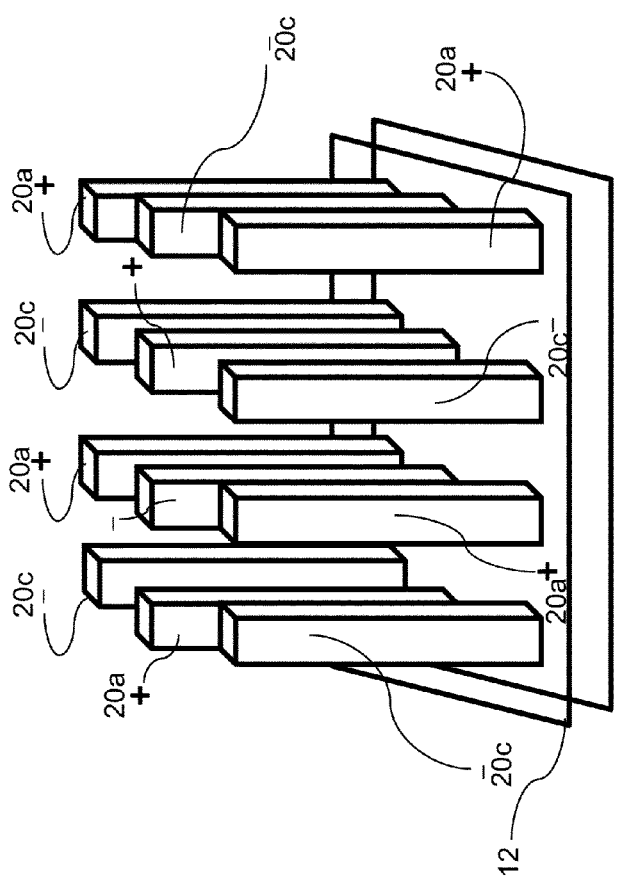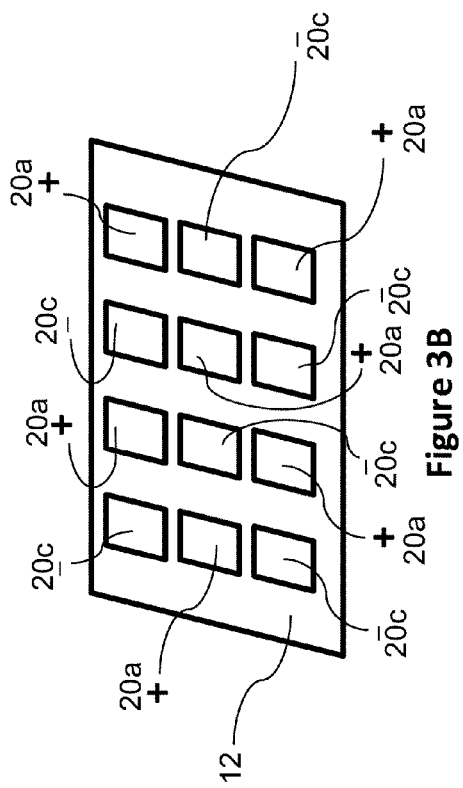

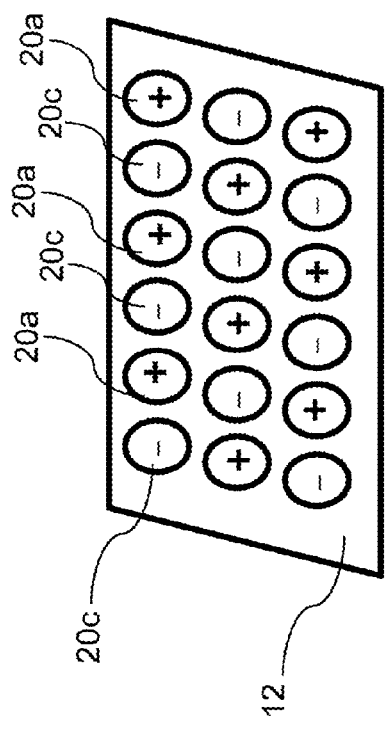
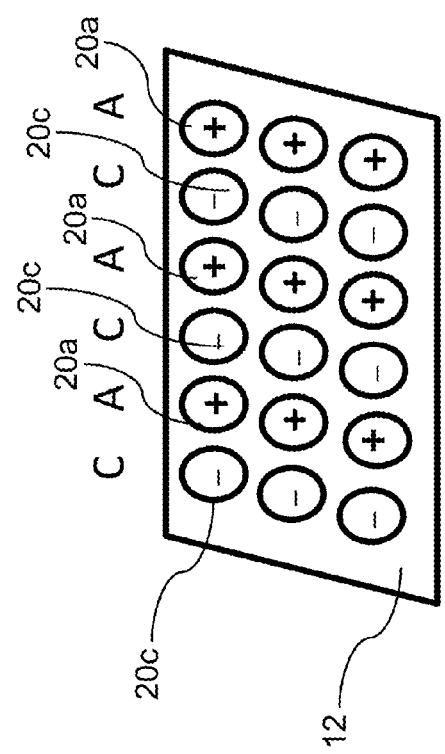

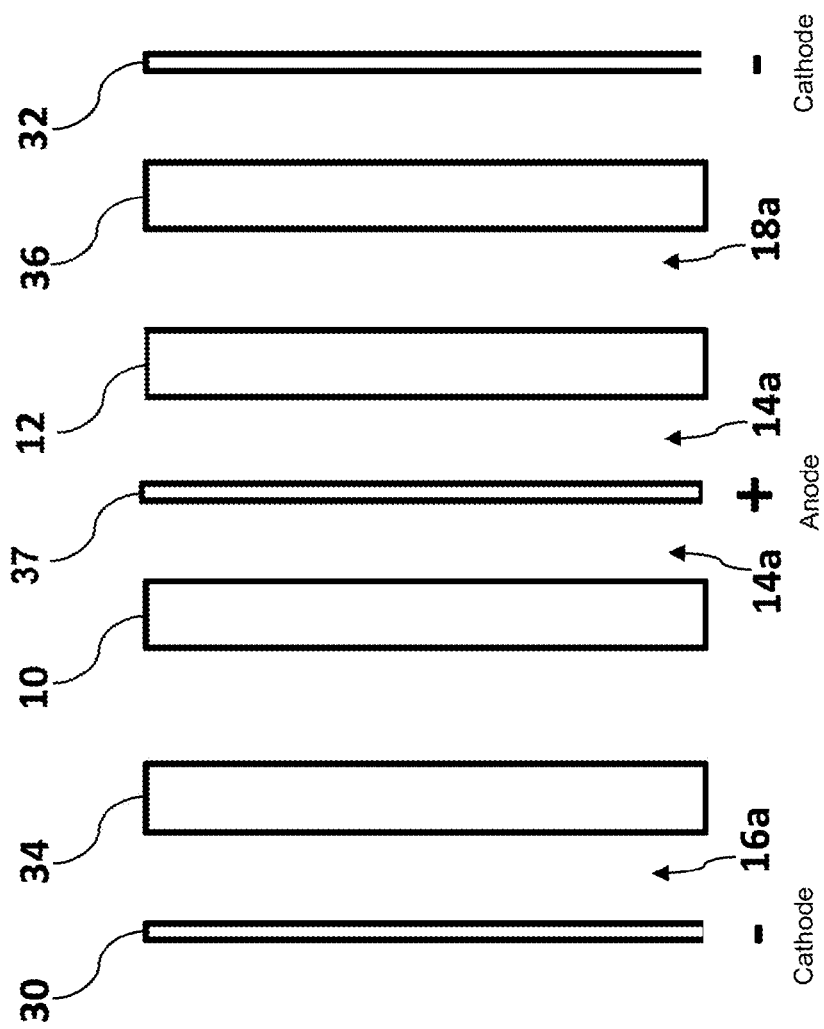

MULTIELECTRODE ELECTROLYTIC DEVICE AND METHOD

BACKGROUND OF THE INVENTION

A sandwich-type electrolytic suppressor comprised of two membranes of the same charge defining three channels is described in U.S. Pat. Nos. 4,999,098 or 5,352,360. The central channel is the sample flow channel while the outside flanking channels are regenerant flow channels. Current is passed between electrodes placed in each of the regenerant flow channels to facilitate generation of electrolysis ions, i.e. hydronium and hydroxide, from the water splitting reaction in the regenerant flow channels. Ion exchange screen typically of the same charge as the membrane ion exchange screens, are placed in each of the three channels. An aqueous eluent liquid stream of sample containing analyte ions to be separated of one charge, positive or negative, flows in an aqueous eluent through the sample flow channel. The electrolysis ions exchange for the eluent counter-ions to the sample analyte ions, thus converting the eluent to a suppressed (weakly ionized) form. The sample analyte counter-ions are also exchanged for electrolysis ions. For example, for anion analysis with sodium hydroxide as the eluent, the sodium ions (the sample counter-ions) are exchanged with hydronium ions thereby converting sodium hydroxide to water. In the above setup, the suppressor supplies hydronium ions at the anode which flow through the adjacent negatively charged sulfonated membrane to remove the sodium ions in the sample stream on to the cathode side. This electrolytic suppressor has directionality in terms of ion removal. In other words, the ionic movement is in one direction from the anode to the cathode for anion analysis.

SUMMARY OF THE INVENTION

One embodiment of the invention is an electrolytic device comprising: (a) a central sample flow channel having an inlet and an outlet; (b) a first regenerant flow channel having an inlet and an outlet; (c) a second regenerant flow channel having an inlet and an outlet; (d) a first charged barrier having exchangeable ions capable of passing ions of one charge, positive or negative, and of blocking bulk liquid flow, disposed between said sample flow channel and first regenerant flow channel; (e) a second charged barrier having exchangeable ions capable of passing ions of the same charge, positive or negative as said first charged barrier exchangeable ions, and of blocking bulk liquid flow, disposed between said sample flow channel and said second regenerant flow channel; (f) a first pair of first and second spaced electrodes disposed in said first regenerant flow channel; and (g) a second pair of third and fourth spaced electrodes disposed in said second regenerant flow channel.

In another embodiment, the above electrolyte device is used in an electrolytic method (e.g., suppression). The method comprises: (a) passing a current between the first and second electrodes of opposite charge to each other; (b) passing a current between the third and fourth electrodes of opposite charge to each other; and (c) flowing an aqueous liquid stream containing sample through the sample flow channel.

A second embodiment of an electrolytic device according to the invention comprises: (a) a central sample flow channel having an inlet and an outlet; (b) a first electrode disposed in said central sample flow channel; (c) a first regenerant flow channel having an inlet and an outlet; (d) a second regenerant flow channel having an inlet and an outlet; (e) a first charged barrier having exchangeable ions capable of passing ions of one charge, positive or negative, and of blocking bulk liquid flow, disposed between said sample flow channel and first regenerant flow channel; (f) a second charged barrier having exchangeable ions capable of passing ions of the same charge, positive or negative, as said first charged barrier exchangeable ions, and of blocking bulk liquid flow, disposed between said sample flow channel and said second regenerant flow channel; and (g) second and third electrodes disposed in said first and second regenerant flow channels, respectively.

In another embodiment, the second electrolyte device is used in an electrolytic method comprising: (a) passing current between said first and second electrodes having opposite polarity to each other and between said first and third electrodes having opposite polarity to each other, said second and third electrodes being of the same polarity; and (b) flowing an aqueous liquid stream containing sample through said sample flow channel.

BRIEF DESCRIPTION OF THE DRAWINGS

FIGS. 3A and 3B, are top and bottom views, respectively, of rectangular electrode configuration of the device of FIG. 1.

FIGS. 4A and 4B show circular electrode configurations of the device of FIG. 1 with different polarities.

FIG. 8 shows a device of the present invention with a three electrode configuration as per the present invention.

Like reference numerals refer to corresponding parts throughout.

DETAILED DESCRIPTION OF EMBODIMENTS

In one embodiment, the electrolytic device of the present invention is used as an electrolytic suppressor in a suppressor ion chromatography system. The purpose of a suppressor is to reduce the conductivity and noise of the analysis stream background while enhancing the conductivity of the analytes (i.e., increasing the signal/noise ratio), while maintaining chromatographic efficiency.

Figure 1:
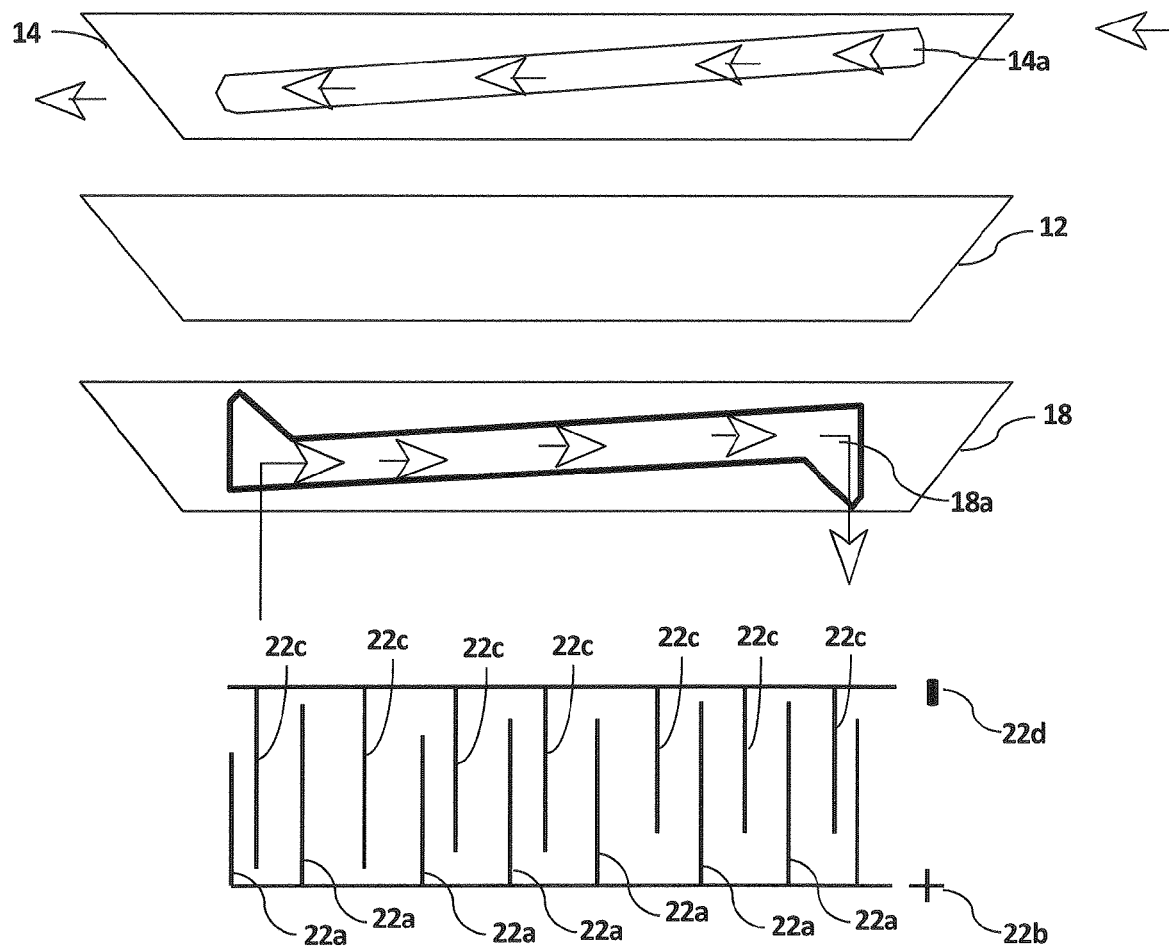
FIG. 1 is a schematic view of a two channel embodiment of the electrolytic device of the present invention.

A simplified apparatus for performing the present invention is similar to the suppressed ion chromatography system illustrated in FIG. 1 of U.S. Pat. No. 5,352,360, incorporated by reference. The system includes a chromatographic separator, typically in the form of a chromatographic column packed with chromatographic separation medium. In one embodiment, such medium is in the form of a packed bed of ion-exchange resin. In another embodiment, the separation medium is a porous hydrophobic chromatographic resin with essentially no permanently attached ion-exchange sites. Another system is used for mobile phase ion chromatography (MPIC) as described in U.S. Pat. No. 4,265,634. An ion exchange site-forming compound, including hydrophobic portion and an ion-exchange site, is passed through the column and is reversibly adsorbed to the resin to create ion-exchange sites.

As shown in FIG. 1 of the '360 patent, arranged in series with the chromatography column is a sandwich membrane suppressor serving to suppress the conductivity of the electrolyte of the eluent to a weakly ionized form from the column but not the conductivity of the separated ions.

The effluent from the suppressor is directed to a detector, preferably in the form of a flow-through conductivity cell, for detecting all the resolved (separated) ionic species therefrom. A suitable sample, e.g. containing analyte anions for anion analysis, is supplied through a sample injection valve and is passed through the system in a solution of eluent, e.g. an aqueous solution of a base such as sodium hydroxide from an eluent source, e.g. a reservoir, drawn by a pump. The eluent liquid stream may include sample analyte and a developing reagent electrolyte. An example of the developing reagent electrolyte may be cation hydroxide. The chromatography effluent solution leaving the separation column is directed to the suppressor wherein the electrolyte is suppressed, i.e., converted to a weakly conducting ionized form. After suppression, the chromatography effluent with separated ionic species passes through the conductivity cell.

In the conductivity cell, the presence of ionic species produces an electrical signal proportional to the amount of ionic material. Such signal is typically directed from the cell to a conductivity meter, thus permitting detection of the concentration of separated ionic species.

The effluent from the conductivity cell may be directed to flow-through detector effluent channels flanking the sample flow channel in a sandwich membrane suppressor. The suppressor will be described in detail hereinafter. The detector effluent may flow through a splitter valve or tee which separates the detector effluent into two different conduits and to supply the detector effluent to the detector effluent flow-through channels of the suppressor and then to waste. Alternatively, the detector effluent may flow through the detector effluent chambers sequentially then to waste. The chromatography effluent flows from the chromatographic column to the suppressor, and from the suppressor device to the conductivity detector.

Referring to FIGS. 2-5 of the '360 patent, a device is illustrated in the form of a sandwich suppressor including a central chromatography effluent flow channel defined on both sides by ion-exchange membranes to the exterior of which are two flanking detector effluent flow channels. The suppressor includes a chromatography effluent flow channel in the form of a chromatography effluent compartment, partially bounded by a chromatography effluent gasket defining a central cavity. Flow-through ion-exchange material in the form of a chromatography effluent screen, not shown, is disposed in the cavity. Membrane sheets and are mounted to extend along opposite sides of chromatography effluent screen and, together with the gasket, define the outer perimeter of the chromatography effluent flow channel. The ion-exchange membrane sheets may be of a type such as disclosed in the '360 patent. Openings are provided for effluent inlet and outlet to the effluent flow channels. The membrane sheets may be replaced by any barriers which include exchangeable ions capable of passing ions of one charge, positive or negative, and which are capable of blocking bulk liquid flow.

In the device of the '360 patent, detector effluent gaskets are mounted to the facing surfaces of the membrane sheets and define detector effluent flow channels. Flow-through material may be provided in the detector effluent flow channels, e.g. in the form of charged or uncharged screens. Openings are provided for inlet and outlet detector effluent flow through the detector effluent gaskets.

The structure and function of the electrolytic device of the present invention may be generally the same as the structure and function of the sandwich-type suppressor of FIG. 2-5 of the '360 patent, incorporated by reference, except that for the structure and function of the electrodes. As set forth above, in sandwich suppressor of the '360 patent, the ion removal is directional, i.e., the ions flow from one electrode to the other across the membranes defining the sample flow channel. The net effect of this flow of ions is the eluent counterions (e.g., $Na^+$) are drawn across only one membrane. In contrast, the devices of the present invention that have two membranes on opposing sides of the sample flow channel will have a flow of eluent counter ions across both of these two membranes from the sample flow channel.

One benefit of a lack of directionality is that the device is more uniform in terms of ionic forms and associated swelling. Ion exchange materials swell differently in the acid versus salt forms. In the electrolytic suppressor of the '360 patent, due to the directionality there are differential swelling and differential flow characteristics in the two regenerant channels. In the recycle mode these swelling differences can impact the flow through each channel particularly when the flow is split and each channel is fed with a split flow.

Figure 2:
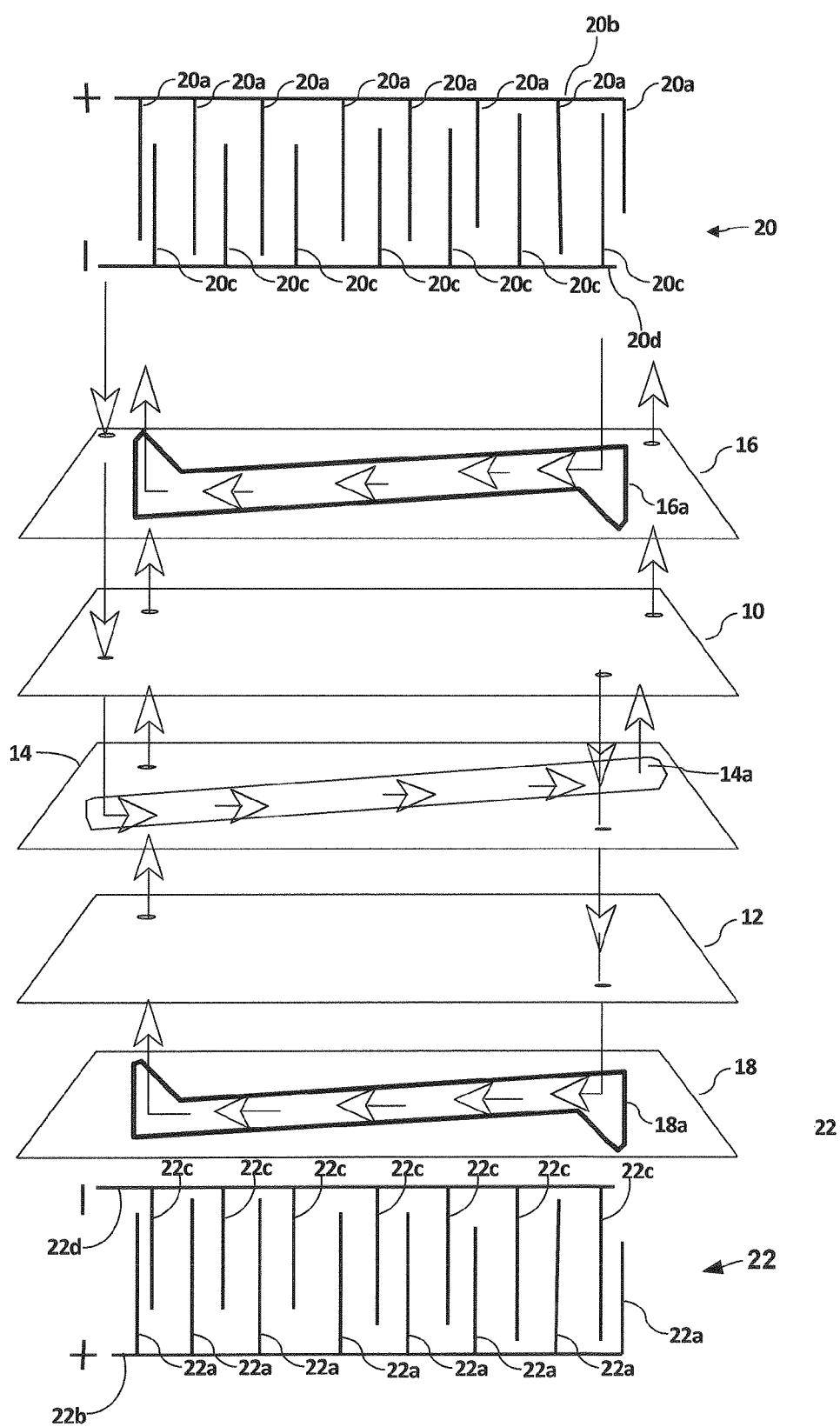
FIG. 2 is a schematic view of a three channel embodiment of the electrolytic device of the present invention.

In one embodiment of the electrolytic device of the present invention shown in FIGS. 1 and 2 herein, the electrodes are arranged in a clasped finger-like pattern. This arrangement facilitated the regeneration of the suppressor in smaller areas between the various anodes and the cathodes. The electrode arrangement also permits the use of a single power supply. Further, this suppressor does not have directionality in terms of ionic movement since the eluent counter ions would be drawn in opposite direction across the two membranes. This leads to more even swelling in the two regenerant channels. This is particularly advantageous when using recycle in which the flow in the two legs of the regenerant channels are expected to be nearly identical. Also, since the electrodes within a particular regenerant channel are in close proximity to each other, the regeneration is expected to be more efficient. The resistance of the device is low since the electrodes are in close proximity.

Referring to FIG. 1, a two-channel device is illustrated suitable for use as a suppressor. Electrode arrays 22 are in the form of inert metal conductors (e.g. platinum wires) arranged in an inter-leaved or clasped finger-like configuration. Electrode arrays 22 protrude into the regenerant flow channel 18a of gasket 18. The gasket may be constructed as illustrated in the '360 patent. The electrodes 22a and 22c are connected to the anode (22b) and cathode (22d) of a DC power supply (not shown).

As illustrated in FIG. 1, array 22 includes a first set of electrodes 22a (e.g. in the form of platinum wires) connected to a common electrically conductive support electrode wire 22b in electrical communication with one terminal of a DC power source and further include a second set of electrodes 22c connected to a common electrically conductive support electrode wire 22d connected to the other terminal of the power source. Each pair of adjacent spaced electrodes 22a and 22c form an electrode pair. In operation, electrodes 22a and 22c are of opposite charge. As illustrated, electrodes 22a are positively charged and electrodes 22c are negatively charged. Each adjacent set of inter-leaved electrodes in the array constitutes an electrode pair. Preferably, array 22 includes multiple electrode pairs, e.g. 2, 3, 4 or more electrode pairs. However, the invention encompasses the use of only a single electrode pair in each of the regenerant flow channels.

The device of FIG. 1 comprises an ion exchange barrier 12 which defines two channels, an eluent channel 14a defined by a gasket 14 and a regenerant channel 18a defined by gasket 18. The gaskets comprise of optional ion exchange screens and the exposed ion exchange surfaces are available in the channels 14a and 18a for transport. It is also possible to define the channels using hardware comprising of PEEK plates.

In operation, for anion analysis, all the ion exchange materials in the electrolytic device are cation exchange, i.e. have exchangeable cations, including membrane 12. Regenerant channel 18a may or may not include ion exchange materials (e.g. screens with exchangeable cation exchange moieties). Central sample flow channel 14a is defined by membranes 12 with the regenerant channel 18a flanking the outside of the membrane. Charged screens, not shown, may be included in sample flow channel 14a. When a cation hydroxide, e.g. sodium hydroxide, eluent flows into the sample flow channel 14a, the cations (e.g. sodium ions) for anion analysis are exchanged on available ion exchange surfaces (if present in the form of screens) and on ion exchange membrane 12 resulting in formation of deionized water. The exchanged sodium ions eventually appear in the regenerant channel 18a. Hydronium ions generated at the anode 22a are driven towards the cathodes 22c. In this process, the sodium ions are replaced with hydronium ions thus regenerating the ion exchange sites on membranes 12. Sodium ions are ultimately driven out of sample flow channel 14a into regenerant channels 18a and are converted to sodium hydroxide which flows out the regenerant channels in a countercurrent direction to flow in channel 14a.

Referring to FIG. 2 herein, a three-channel device is illustrated which is similar to the two-channel device of FIG. 1. Electrode arrays 20 and 22 are illustrated in the form of inert metal conductors (e.g. platinum wires) arranged in the inter-leaved or clasped finger-like pattern shown in FIG. 2 to be described in more detail. Electrode arrays 20 and 22 in one embodiment can protrude into the regenerant flow channel 16a of gasket 16 and into channel 18a of gasket 18, respectively. The gaskets may be constructed as illustrated in the '360 patent. The electrodes are connected to the anode and cathode of a DC power supply (not shown).

As illustrated in FIG. 2, array 20 includes a first set of electrodes 20a (e.g. in the form of platinum wires) connected to a common electrically conductive support electrode wire 20b in electrical communication with one terminal of a DC power source and further include a second set of electrodes 20c connected to a common electrically conductive support electrode wire 20d connected to the other terminal of the power source. Each pair of adjacent spaced electrodes 20a and 20c form an electrode pair. In operation, electrodes 20a and 20c are of opposite charge. As illustrated, electrodes 20a are positively charged and electrodes 20c are negatively charged. Each adjacent set of inter-leaved electrodes in the array constitutes an electrode pair. Preferably, array 20 includes multiple electrode pairs, e.g. 2, 3, 4 or more electrode pairs. However, the invention encompasses the use of only a single electrode pair in each of the regenerant flow channels. Array 22 is of the same type as array 20 with elements 22a, 22b, 22c and 22d of the same type as elements 20a, 20b, 20c and 20d.

In operation, for anion analysis, all the ion exchange materials in the electrolytic device are cation exchange, i.e. have exchangeable cation, including membranes 10 and 12 and an optional screen, not shown, in channel 14. Regenerant channels 16a and 18a may or may not include ion exchange materials (e.g. screens with exchangeable cation exchange moieties and/or cation exchange resin). Central sample flow channel 14a is defined by membranes 10 and 12 with the regenerant channels 16a and 18a flanking the outside of the membranes. Charged screens, not shown, may be included in sample flow channel 14a. When a cation hydroxide, e.g. sodium hydroxide, eluent flows into the sample flow channel 14a, the cations (e.g. sodium ions) for anion analysis are exchanged on membranes 10 and 12 resulting in formation of deionized water. The exchanged sodium ions are driven in both directions towards the cathodes 20c and 22c in the regenerant channels 16a and 18a. Hydronium ions generated at the anodes 20a and 22a are driven towards the cathodes 20c and 22c. The sodium ions are replaced with hydronium ions thus regenerating the ion exchange sites on membranes 10 and 12. Sodium ions are driven out of sample flow channel 14a into regenerant channels 16a and 18a and are converted to sodium hydroxide which flows out the regenerant channels in a countercurrent direction to flow in channel 14a. The minimum spacing between the cathode 20c and the anode 20a may range from about 0.001" to 2" and preferably from about 0.03" to 0.3". This spacing may also be used with respect to cathode 22c and anode 22a.

Benefits of the present device over the prior art devices include more uniform and more efficient regeneration of the ion exchange membranes 10 and 12. Also, there is no gas generation in sample flow in channel 14a. Regenerant channels 16a and 18a have both hydrogen and oxygen gases which can be removed by a gas removal device. According to the present invention, it is advantageous to regenerate smaller sections of a device rather than regenerating the entire device. The electrodes in both regenerant channels may be powered by a single power supply or by an array of batteries or power supplies. The device may be configured in parallel such that 20a and 22a are both electrically connected to one output of the power supply and that 20c and 22c are also both electrically connected to different output of the power supply.

In another embodiment, more than one power supply may be used. For example, a first power supply can be electrically connected to the cathode and the anode of regenerant channel 16a and a second power supply can be electrically connected to the cathode and the anode of regenerant channel 18a. In an alternative embodiment, the power supply may be configured to apply a voltage that results in a current flowing between two electrodes.

It should be noted that a substantial portion of the current flows between 20a and 20c, and also between 22a and 22c because of the relatively low resistance in the gap between electrodes in a particular regenerant channel. The invention is also applicable to cation analysis. There, the polarities of the elements of the electrolytic device would be reversed.

FIG. 3A shows an array of rectangular electrode pairs (20a and 20c), of a particular configuration making contact with the ion exchange screen or membrane on the regenerant channel 18a. The proximity of the electrodes facilitates regeneration of the ion exchange screen and membranes. FIG. 3B shows a bottom view of the electrodes on top of the membrane 12 or of screens, not shown. The purpose of the close placement to the membranes or screens, or direct contact therewith, is to facilitate regeneration of the ion exchange surface. When the electrode pairs are connected to a power supply, not shown, the illustrated electrode pairs in the array are of alternate charges in each row of electrodes.

FIG. 4A shows circular electrodes in the same spatial relationship and polarity alignment as FIG. 3A. Similar to FIG. 3A the electrodes make contact with the regenerant screens or the ion exchange membrane in the regenerant channel. The proximity of the electrodes of opposite polarity ensures good regeneration of the ion exchange surfaces. In operation for anion analysis the hydronium ions generated electrolytically are driven using the ion exchange medium (screen and/or membrane) towards the cathode. In this process, that section of the ion exchange surface (screen and/or membrane) is regenerated. At the cathode, the hydroxide ions generated electrolytically are available to react with the transported hydronium ions and forms water. Eluent counterions when present are also driven towards the cathode in this example and leave the electrode as a base. Further ion exchange is effected due to the flow of the regenerant and further regeneration occurs. For example the base that is removed into solution can exchange the eluent counterions with the vicinity hydronium ions thus effecting suppression. This ensures that the eluent counterions are removed from the regenerant channel. In essence, this results in suppression of the eluent and conversion of the analyte to the conductive form.

FIG. 4B shows a preferred orientation of the electrodes to facilitate complete regeneration with tandem lines of cathodes adjacent tandem lines of anodes. The benefit of this design is more even regeneration within the suppressor regenerant channel. Preferably the outlet end of the eluent channel is close to the anode region of the electrode. This ensures complete conversion of the analyte to the suppressed form. The reactions occurring at the anode and cathode are similar to the ones described for FIG. 4A. The regenerant flow is from the anode section to the cathode section to ensure complete removal of the base and to ensure that the analyte ions are detected in the conductive form.

Figure 5A:
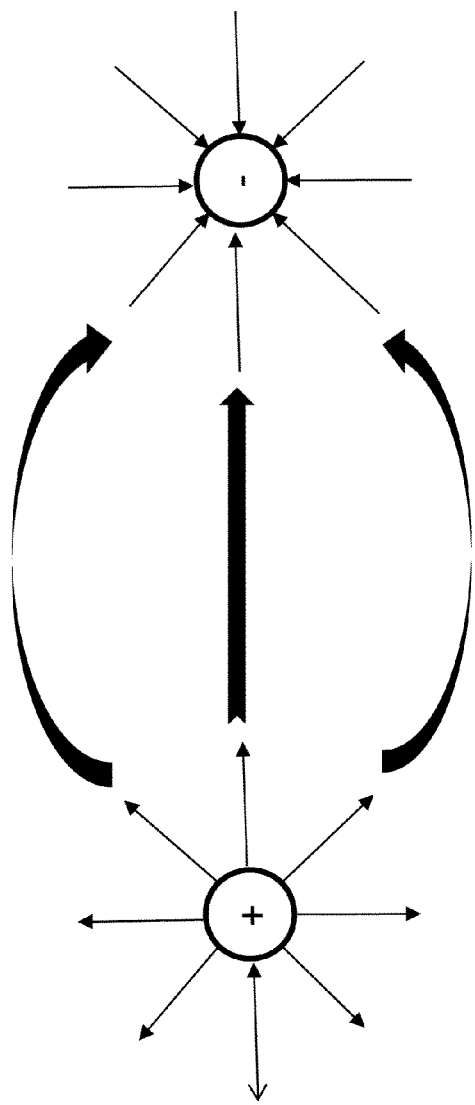
FIGS. 5A and 5B show electrode field lines for electrodes according to the invention.

FIG. 5A shows two point charges in space and the respective electric field lines between the two charges. By convention, the field lines are drawn from a positive charge in space hence the lines are shown emanating from the positive charge and towards the negative charge.

Figure 5B:
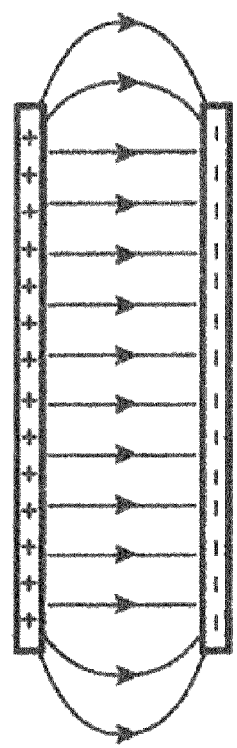

FIG. 5B shows two electrodes and their respective field lines. The field lines define the transport pathway of charges or ions in an electric field. The ions in the vicinity of the electrode will be drawn to the electrode with the opposite polarity following the field lines. The stronger field lines will have higher transport compared to the weaker field lines. The illustrated embodiments of the present invention use this configuration. The ion exchangers in the present invention provide transport pathways for the ions. For example, during anion analysis in a suppressor configuration the ion exchangers are of cation exchange functionality and transport cations. In this embodiment the eluent and sample cations are routed towards the opposite polarity electrode, namely the cathode, following the field lines as illustrated in FIG. 5B. The cations are removed via cation exchange membranes resulting in suppression of the eluent to a weakly ionized form. The hydronium ions required for this reaction are transported also across the ion exchange membranes and also follow the field lines emanating from the anode and towards the cathode.

Figure 6A:
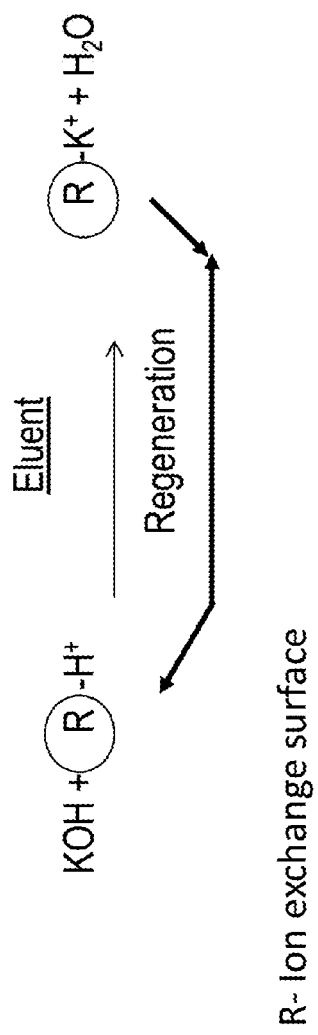
FIG. 6A shows the exhaustion and regeneration cycle of a cation exchange surface and 6B shows electrolysis reactions for the device of FIGS. 1 and 2.
Figure 6B:
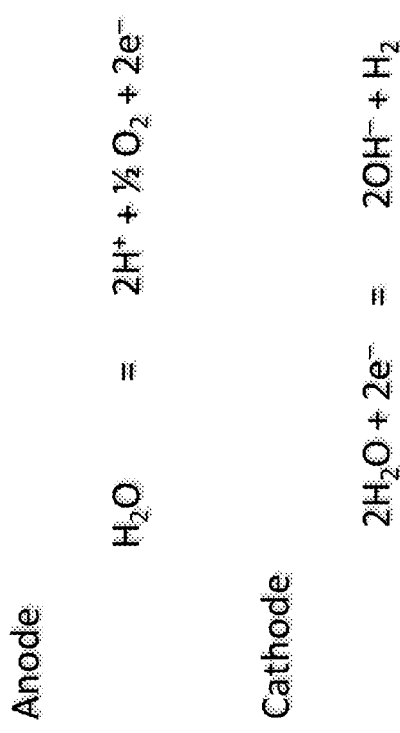

FIG. 6A shows the depletion and regeneration of the ion exchange surface. The electrolysis reactions are also depicted showing formation of the regenerant ions in FIG. 6B. FIG. 6A illustrates a suppressor embodiment for anion analysis. The cation exchange functionalities exchange the counter ion hydronium for the eluent counterions shown as potassium in this example. The net effect of this exchange is that the ion exchange functionality is converted to the potassium form. For a continuously regenerated suppressor device this potassium is converted to the regenerated hydronium form. This ensures that the suppressor reactions occur continuously without any down time. To effect this electrolysis generated ions are supplied to regenerate the ion exchange functionality. Electrolysis is a reaction that occurs on an electrode surface with water present and when the voltage exceeds the water splitting potential which is approximately about 1.5 v. Under these conditions at the anode, hydronium ions are formed and at the cathode hydroxide ions are formed as shown in FIG. 6B. In the above suppressor device for anion analysis the hydronium ions generated from electrolysis are driven by the applied potential towards the cathode. In this process the ion exchange surfaces are regenerated. Any eluent counterion present as exchangeable ions are also driven towards the cathode and exit the device as a base. The exchange reaction results in suppression of the eluent.

Figure 7A:
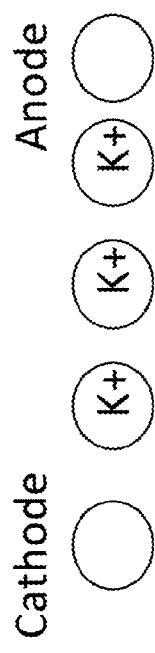
FIGS. 7A, 7B, and 7C show a schematic of ion exchange depletion and regeneration for a cation exchange surface for the electrolytic device of FIGS. 1 and 2 according to the invention.
Figure 7B:
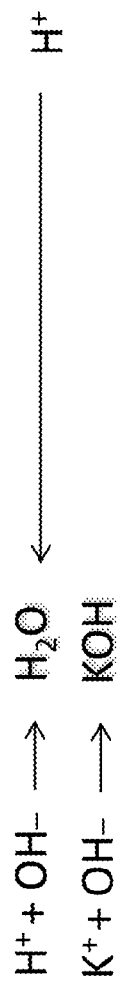
Figure 7C:
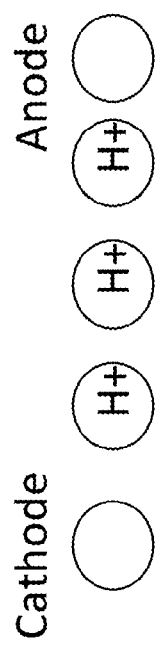

FIG. 7A shows the depleted ion exchange surface in the eluent counterion form, potassium for anion analysis. FIG. 7B shows how the electrolysis generated ions are used in the suppression reaction. The generated hydronium ions and potassium ions are driven towards the cathode. At the cathode the transported cations combine with the electrolytically generated hydroxide ions to form water and potassium hydroxide as shown in FIG. 7B. FIG. 7C shows a fully regenerated ion exchange surface. In practice, the ion exchange is continuously depleted and regenerated.

The net effect is conversion of the ion exchange surface to the hydronium ion or fully regenerated form. Having an array of electrodes allows for the regeneration function to occur in small areas of the ion exchange surface thereby regenerating the entire surface. The flow allows for the transport of the removed ions and facilitates more ion exchange on the ion exchange surface. The close proximity of the electrodes allows for regeneration without formation of significant wattage or heat. An array of electrode pairs allows complete regeneration of the ion exchange surface.

In another embodiment (not shown) the electrodes are an array of electrodes that are point anodes or cathodes this way the entire surface of the suppressor could be regenerated more efficiently. It should be noted that although it is advantageous to power the device with one power supply, it is feasible to regenerate the various sections using individual power supplies. The concentration of the electrolysis ions are directly proportional to the current applied. Therefore when regenerating large surfaces the current required would also be significantly large and therefore necessitating the need to use multiple power supplies.

Another embodiment of the present invention shown in FIG. 8 is an electrode arrangement that simulates a chemical suppressor in ionic directionality. The sodium ions are driven simultaneously to the cathode 30 and 32 in the regenerant channels 16a and 18a. Oxygen gas is formed at the anode and so a gas removal device is preferably used to remove the gas prior to detection by a conductivity detector.

Referring again to FIG. 8, the structure of the electrolytic device is the same as that of FIG. 2 and for the suppressor of the '360 patent except for the electrodes. Charged screens 34 and 36 are illustrated in channels 16a and 18a, respectively and may be of the type illustrated in the '360 patent for the sandwich suppressor of FIGS. 2-5. Also, electrodes 30 and 32 shown in channels 16a and 18a may be of the same type as the ones illustrated in FIGS. 2-5 of the '360 patent except for their polarities as explained. As in the embodiment of FIG. 8 charged screens 34 and 36 have exchangeable ions of the same charge. In contrast to the sandwich suppressor of FIGS. 2-5 of the '360 patent, the electrolytic device of this embodiment has a third electrode 37 disposed in the sample eluent flow channel 14a between membranes 10 and 12. In operation for anion analysis, electrodes 30 and 32 are negatively charged (cathodes) and electrode 37 is positively charged (anode). Thus, the cation counter-ions to the sample (e.g. sodium for sodium hydroxide eluent) are drawn across membranes 10 and 12 toward cathodes 30 and 32 in channels 16a and 18a, respectively, for non-directional flow (i.e. equal flow across membranes 10 and 12) with the advantages set forth above. A single power supply may be used. This embodiment of the invention also is applicable to cation analysis by reversal of the polarities of the components of the electrolytic device.

The electrolytic device of the present invention has been illustrated for use as a suppressor in suppressed ion chromatography. However, it could also be used for other purpose such as a pretreatment device before chromatography as set forth in U.S. Pat. No. 5,518,622 or as a post-treatment device, e.g. after chromatography. The electrode configuration of the present device could also be used to regenerate devices of the prior art such as a continuously regenerated trap column, a water purifier and the like.

In order to illustrate the invention, the following non-limiting examples of its practice are provided.

EXAMPLES

Example 1

Figure 9:
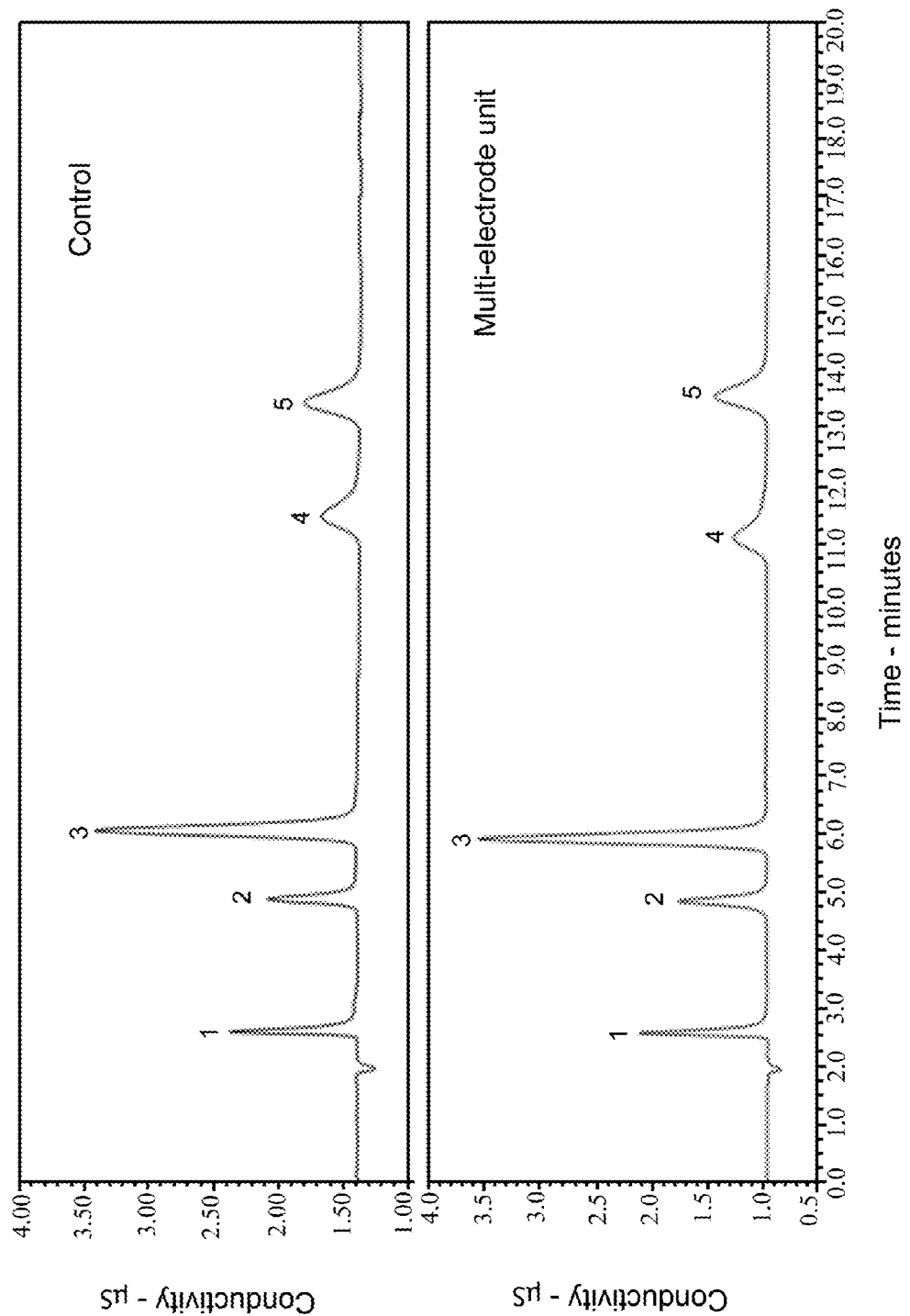
FIGS. 9 and 10 show experimental results using the electrolytic devices of the present invention.

An anion suppressor device of FIG. 2 was assembled and powered by a Hewlett Packard power supply. The performance of this suppressor was compared to the performance of a commercial ASRS 300 suppressor from Thermo Scientific. A Thermo Scientific Dionex ICS-3000 system was used in this work. A 4×250 mm IonPac AS15 column was used for the analysis with 38 mM KOH at 1.2 mL/min. A test mixture comprising of five anions was analysed and showed comparable performance in terms of efficiency, peak shapes, peak response and noise to a standard suppressor (labeled as "Control") as shown in the chromatogram of FIG. 9. Excellent performance of the suppressor of FIG. 2 (see chromatogram labeled "Multi-electrode unit" of FIG. 9) was established.

Example 2

Figure 10:
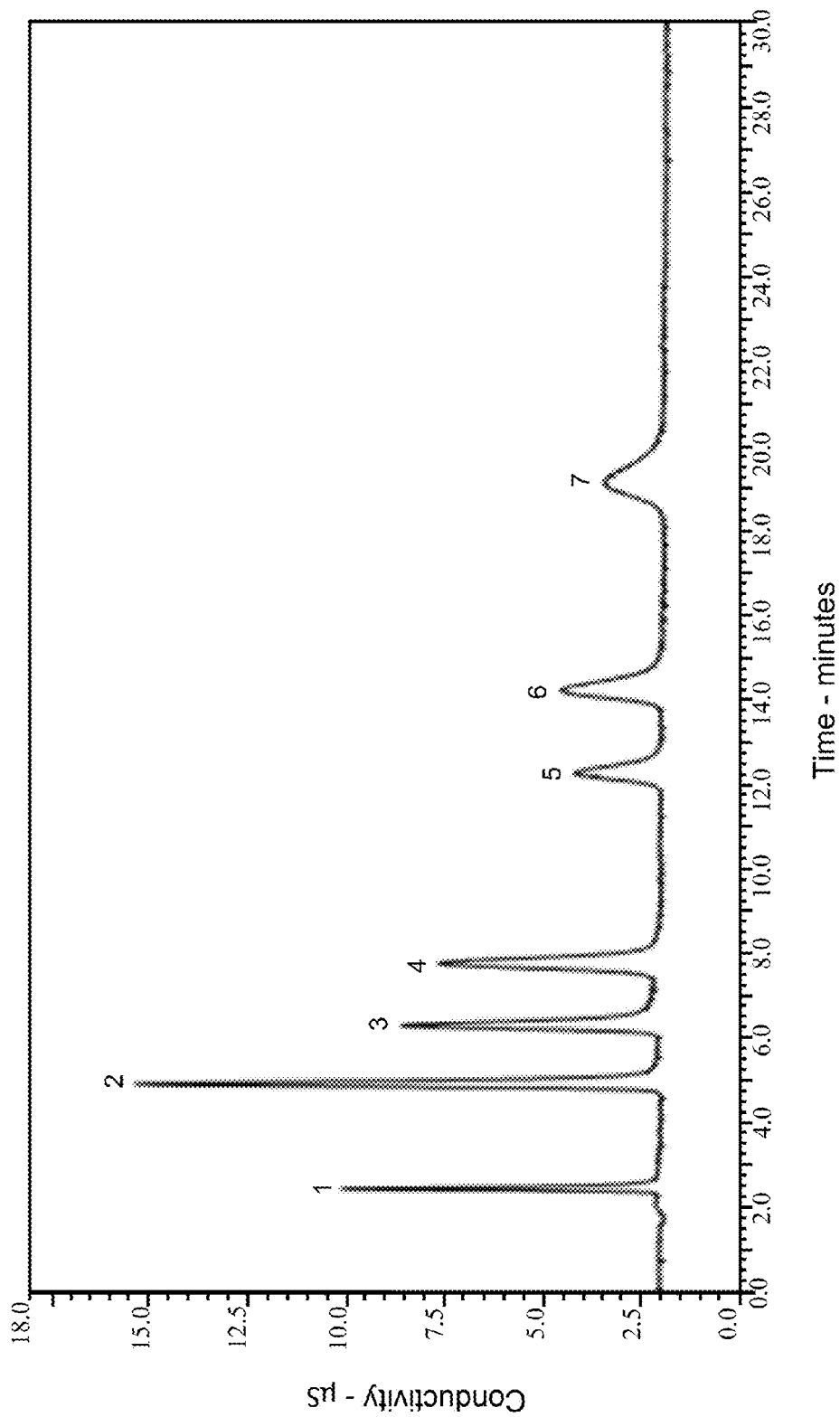

This Example shows the analysis of 7 inorganic anions using a 4-mm AS15 column with 38 mM KOH at 1.2 mL/min. A Thermo Scientific Dionex ICS-3000 system was used in this work. The suppressor device of FIG. 8 was assembled. The electrode inside the eluent channel was connected to the anode and the two electrodes residing inside the regenerant channels were connected to the cathode. The unit was powered at 113 mA. The effluent exiting the suppressor passed through a gas removal device, Dionex CRD 200 4-mm unit before entering the detector cell. The CRD 200 4-mm unit was operated under vacuum mode for gas removal. FIG. 10 shows the chromatogram obtained with this set up and the presence of Fluoride (1), Chloride (2), Nitrite (3), Sulfate (4), Bromide (5), Nitrate (6) and Phosphate (7) were identified. The suppressor of FIG. 7 also does not show directionality in terms of ion transport. The eluent cations were removed in this setup across both membranes and good suppression was established.

What is claimed is:

1. An electrolytic device comprising:
   (a) a sample flow channel having an inlet and an outlet;
   (b) a first regenerant flow channel having an inlet and an outlet;
   (c) a first charged barrier having exchangeable ions capable of passing ions of one charge, positive or negative, and of blocking bulk liquid flow, disposed between said sample flow channel and first regenerant flow channel; and
   (d) a first pair of first and second spaced electrodes disposed in said first regenerant flow channel.

2. The electrolytic device of claim 1 further comprising
   (e) a second regenerant flow channel having an inlet and an outlet;
   (f) a second charged barrier having exchangeable ions capable of passing ions of one charge, positive or negative; and of blocking bulk liquid flow, disposed between said sample flow channel and said second regenerant flow channel; and
   (g) a second pair of third and fourth spaced electrodes disposed in said second regenerant flow channel.

3. The electrolytic device of claim 2 in which the exchangeable ions of the second charged barrier are of the same charge, positive or negative, as the exchangeable ions of the first charged barrier.

4. The electrolytic device of claim 2 further comprising a third pair of spaced electrodes in said first regenerant flow channel forming a first array with said first pair of spaced electrodes, and a fourth pair of spaced electrodes in said second regenerant flow channel forming a second array with said second pair of spaced electrodes.

5. The electrolytic device of claim 2 in which said first and second pairs of spaced electrodes are connected to the same power source.

6. The electrolytic device of claim 1 in the configuration of a suppressor in a suppressed ion chromatography system, said system comprising:
   (e) a chromatography separator having an inlet and an outlet, said separator outlet being in fluid communication with said sample flow channel inlet.

7. The electrolytic device of claim 2 in which said first and second pairs of electrodes are in contact with said first and second charged barriers, respectively.

8. The electrolytic device of claim 1 further comprising:
   (e) a detector in fluid communication with said electrolytic device.

9. An electrolytic device comprising:
   (a) a central sample flow channel having an inlet and an outlet;
   (b) a first electrode disposed in said central sample flow channel;
   (c) a first regenerant flow channel having an inlet and an outlet;
   (d) a second regenerant flow channel having an inlet and an outlet;
   (e) a first charged barrier having exchangeable ions capable of passing ions of one charge, positive or negative, and of blocking bulk liquid flow, disposed between said sample flow channel and first regenerant flow channel;
   (f) a second charged barrier having exchangeable ions capable of passing ions of the same charge, positive or negative, as said first charged barrier exchangeable ions, and of blocking bulk liquid flow, disposed between said sample flow channel and said second regenerant flow channel; and (g) second and third electrodes disposed in said first and second regenerant flow channels, respectively.

10. The electrolytic device of claim 9 in the configuration of a suppressor in a suppressed ion chromatography system, said system further comprising:

(h) a chromatography separator having an inlet and an outlet, said separator outlet being in fluid communication with said sample flow channel inlet.

11. The system of claim 10 further comprising (i) a detector in fluid communication with said suppressor.

12. An electrolytic method using an electrolytic device comprising a sample flow channel having an inlet and an outlet; a first regenerant flow channel having an inlet and an outlet; a first charged barrier having exchangeable ions capable of passing ions of one charge, positive or negative, and of blocking bulk liquid flow, disposed between said sample flow channel and first regenerant flow channel; and a first pair of first and second spaced electrodes disposed in said first regenerant flow channel; said method comprising:

(a) passing a current between said first and second electrodes of opposite charge to each other; and (b) flowing an aqueous liquid stream containing sample through said sample flow channel.

13. The method of claim 12 in which said electrolytic device further comprises a second regenerant flow channel having an inlet and an outlet; a second charged barrier having exchangeable ions capable of passing ions of one charge, positive or negative; a second pair of third and fourth spaced electrodes disposed in said second regenerant flow channel; said method further comprising:

(c) passing a current between said third and fourth electrodes of opposite charge to each other.

14. The method of claim 13 in which the exchangeable ions of the second charged barrier are of the same charge, positive or negative, as the exchange ions of the first charged barrier.

15. The method of claim 13 in which said first and second electrode pairs are powered by the same power source.

16. The method of claim 12 in which said aqueous liquid stream comprises an aqueous eluent liquid stream including previously separated sample analyte ions in a developing reagent electrolyte and in which ions of said developing reagent of the same charge as said first and second charged barrier exchangeable ions are suppressed in said sample flow channel.

17. The method of claim 12 in which said separated sample analyte ions in said eluent stream are previously separated in a chromatographic separator and said eluent stream then flows into said sample flow channel.

18. The method of claim 13 in which said electrolytic device further comprises a third pair of spaced electrodes in said first regenerant flow channel forming a first array with said first pair of spaced electrodes, and a fourth pair of spaced electrodes in said second regenerant flow channel forming a second array with said second pair of spaced electrodes, said method further comprising passing a current between the electrodes in said third electrode pair and between the electrodes in said fourth electrode pair.

19. The method of claim 17 further comprising detecting said separated sample ions.

20. An electrolytic method using an electrolytic device comprising a central sample flow channel having an inlet and an outlet; a first electrode disposed in said central sample flow channel; a first regenerant flow channel having an inlet and an outlet; a second regenerant flow channel having an inlet and an outlet; second and third electrodes disposed in said first and second regenerant flow channels respectively; a first charged barrier having exchangeable ions capable of passing ions of one charge, positive or negative, and of blocking bulk liquid flow, disposed between said sample flow channel and first regenerant flow channel; and a second charged barrier having exchangeable ions capable of passing ions of the same charge, positive or negative as said first charged barrier exchangeable ions, and of blocking bulk liquid flow, disposed between said sample flow channel and said second regenerant flow channel; said method comprising:

(a) passing current between said first and second electrodes having opposite polarity to each other and between said first and third electrodes having opposite polarity to each other, said second and third electrodes being of the same polarity; and (b) flowing an aqueous liquid stream containing sample through said sample flow channel.

21. The electrolytic method of claim 20 in which said aqueous liquid stream comprises an aqueous eluent liquid stream including previously separated sample analyte ions in a developing reagent electrolyte and in which ions of said developing reagent of the same charge as said first and second charged barrier exchangeable ions are suppressed in said sample flow channel.

22. The electrolytic device of claim 1 further comprising: a power source, in which said first and second spaced electrodes are electrically connected to an anode and a cathode, respectively, of said power source, said power source configured to pass a current between said first and second electrodes so that said first and second electrodes have an opposite polarity to each other.

23. The electrolytic device of claim 2 further comprising: a power source, in which said first and second spaced electrodes are electrically connected to an anode and a cathode, respectively, of said power source; and said third and fourth spaced electrodes are electrically connected to said anode and said cathode, respectively, of said power source, said power source configured to pass a current between said first and second electrodes and between said third and fourth electrodes so that said first and second electrodes have an opposite polarity to each other and said third and fourth electrodes have an opposite polarity to each other.

* * * * *